United States Patent
Williams et al.

(10) Patent No.: US 11,078,142 B2
(45) Date of Patent: *Aug. 3, 2021

(54) PROCESS AND PLANT FOR PRODUCING METHANOL FROM SYNTHESIS GASES HAVING A HIGH PROPORTION OF CARBON DIOXIDE

(71) Applicant: L'Air Liquide, Société Anonyme pour l'Etude et l'Exploitation des Procédés Georges Claude, Paris (FR)

(72) Inventors: Bryce Williams, Frankfurt am Main (DE); Timm Schuhmann, Offenbach (DE); Veronika Gronemann, Karben (DE); Stephane Haag, Frankfurt am Main (DE); Frank Castillo-Welter, Friedrichsdorf (DE)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/996,185

(22) Filed: Aug. 18, 2020

(65) Prior Publication Data
US 2021/0053898 A1   Feb. 25, 2021

(30) Foreign Application Priority Data
Aug. 19, 2019   (EP) .................................. 19020480

(51) Int. Cl.
  *C07C 29/151*   (2006.01)
  *B01J 19/24*    (2006.01)
  *C07C 31/04*    (2006.01)

(52) U.S. Cl.
  CPC ......... *C07C 29/1518* (2013.01); *B01J 19/245* (2013.01); *B01J 19/248* (2013.01); *B01J 2219/0004* (2013.01); *B01J 2219/00006* (2013.01); *B01J 2219/00033* (2013.01); *C07C 31/04* (2013.01)

(58) Field of Classification Search
  CPC ..... C07C 29/1516; C07C 29/15; C07C 31/04; C10G 2/32; B01J 19/245; B01J 2219/00761; B01J 2219/00002; B01J 2219/24
  See application file for complete search history.

(56) References Cited

FOREIGN PATENT DOCUMENTS

| EP | 2 116 295 | 11/2009 |
|----|-----------|---------|
| WO | WO 2015 193440 | 12/2015 |
| WO | WO 2017 167642 | 10/2017 |

*Primary Examiner* — Jafar F Parsa
(74) *Attorney, Agent, or Firm* — Elwood L. Haynes (57) ABSTRACT

The invention relates to a process for producing methanol and to a plant for producing methanol. A first fresh gas suitable for production of methanol and having a high carbon dioxide content is pre-compressed by a first compressor stage to obtain a second fresh gas. The second fresh gas is merged with a recycle gas stream and further compressed to synthesis pressure in a second compressor stage. Catalytic conversion of the thus obtained synthesis gas stream in a plurality of serially arranged reactor stages with intermediate condensation and separation of the crude methanol reduces the recycle gas amount in the synthesis circuit to such an extent that recycle gas may be directly recycled to the second fresh gas stream, thus ensuring that no recycle gas compressor stage is required and that the total compressor power may be reduced.

11 Claims, 2 Drawing Sheets

PROCESS AND PLANT FOR PRODUCING METHANOL FROM SYNTHESIS GASES HAVING A HIGH PROPORTION OF CARBON DIOXIDE

CROSS REFERENCE TO RELATED APPLICATIONS

This application claims the benefit of priority under 35 U.S.C. § 119 (a) and (b) to European Patent Application No. 19020480.0, filed Aug. 19, 2019, the entire contents of which are incorporated herein by reference.

FIELD OF THE INVENTION

The invention relates to a process for producing methanol, to a plant for producing methanol and to the use of the plant according to the invention in a process according to the invention.

BACKGROUND

Methanol is today typically produced from synthesis gas, a mixture of predominantly hydrogen ($H_2$), carbon monoxide (CO) and carbon dioxide ($CO_2$) in the so-called low-pressure process at pressures between 60 and 120 bar. Depending on technology and plant capacity it is either single-stage or two-stage processes that are employed for conversion of the synthesis gas into methanol with high yield in terms of the reactor section of the process.

In the processes used the synthesis gas, which is usually produced at pressures between 20 and 40 bar, is initially brought to the pressure required for the reaction of more than 60 bar via a gas compressor (synthesis gas compressor). The processes are further typically operated with large gas circuits in a so-called synthesis circuit, also known as synthesis loop, in which synthesis gas not converted into methanol in the first reactor pass is recycled to the reactor inlet as recycle gas. The synthesis circuit is required to achieve sufficient synthesis gas conversions and thus overall yields despite the low per-pass conversions.

Depending on the technology, fresh gas composition and reactor system the recycle gas amount is up to 5 times higher than the supplied fresh gas amount from the synthesis gas production. This is the case especially for synthesis gas/fresh gas compositions having a high $CO_2$ content where, compared to rather CO-rich synthesis gases, a markedly lower thermodynamic equilibrium conversion is observed. A dedicated recycle gas compressor is typically used for conveying and compressing the high gas circuit amounts.

A disadvantage of these high recirculation rates is the accumulation of inert constituents, i.e. constituents not convertible under the conditions of the methanol synthesis, such as methane and nitrogen which must be removed from the synthesis circuit as purge gas. This typically also removes hydrogen as well, which requires subsequent recovery at great cost and inconvenience, usually accomplished using a pressure swing adsorption apparatus.

Examples of processes having a synthesis circuit are disclosed in WO 2015/193440 A1, WO 2017/167642 A1 and in EP 2 116 295 A1.

Addition of additional reactor stages including intermediate condensation of the methanol produced per reactor stage makes it possible to increase the per-pass conversion over the total number of the reactor stages and thus to reduce the recirculation rate.

When using a synthesis circuit which delivers large amounts of unreacted synthesis gas, the individual components of the relevant production plant must have correspondingly large dimensions for the large recycle gas flows. This has the result that the total capital expenditure (CAPEX) costs for the plant increase and/or that for large required capacities the dimensions of the reactors, in particular the external diameter, can come up against the transport limitations of the respective plant project. The recompression of the recycle gas to reaction pressure additionally requires an additional compressor unit (recycle gas compressor), thus increasing not only CAPEX costs but also the total required compressor power and thus the operating expenditure (OPEX) costs for the plant.

A high proportion of $CO_2$ and constituents which are inert under the conditions of methanol synthesis, such as methane ($CH_4$) and nitrogen ($N_2$), additionally strengthen this negative effect. The use of a plurality of reactor stages connected in series including intermediate condensation can reduce the proportion of the recycle gas but the number of required process units also increases, thus typically also increasing CAPEX costs. If a synthesis circuit is completely omitted ("once-through" process) the number of required reactors further increases and the omission of the synthesis circuit is thus in turn negatively compensated.

In the course of the discussion about anthropogenic climate change synthesis gases having a high $CO_2$ are being brought into sharper focus. Consideration is thus given for example to utilizing high carbon dioxide off-gases content for producing synthesis gases instead of sequestering these off-gases for example. It is thus conceivable for example to produce synthesis gases from carbon dioxide from off-gases sources by combination with hydrogen from a water electrolysis, wherein the current for the water electrolysis could derive from renewable energy sources. Such a synthesis gas may be regarded as climate neutral yet contains only very little, if any, carbon monoxide.

As mentioned hereinabove high carbon dioxide proportions in the synthesis gas result in a high recirculation rate based on the synthesis circuit which increases the CAPEX and OPEX costs of the plant. Compensating by introducing a plurality of reaction stages is only partially possible since this approach also increases CAPEX costs.

The synthesis of methanol from carbon dioxide and hydrogen further generates water according to the reaction equation $$CO_2 + 3H_2 \rightleftharpoons CH_3OH + H_2O$$

which is not the case in the conversion of carbon monoxide with hydrogen to afford methanol according to the reaction equation $$CO + 2H_2 \rightleftharpoons CH_3OH.$$

Especially when using high recirculation rates the accumulation of water in the reactor results in successive deactivation of the usually copper-based catalyst used in the methanol synthesis. The use of a plurality of serially arranged reactor stages with intermediate condensation of methanol and water makes it possible to reduce this effect by reducing the water partial pressure in the catalyst bed. However, as mentioned above, the use of a plurality of reactor stages causes the CAPEX costs of the relevant plant to increase.

For synthesis gases comprising exclusively or mainly carbon dioxide as the reactive carbon component and hydrogen it is customary to set a stoichiometric or slightly superstoichiometric ratio in the fresh gas. The stoichiometry number SN, defined as $$SN = \frac{n(H_2) - n(CO_2)}{n(CO) + n(CO_2)}, \text{ with } n \text{ in [mol]},$$

is accordingly 2 to 2.05. Assuming the employed synthesis gas contains no carbon monoxide 3 to 3.05 mol of hydrogen ($H_2$) are therefore required per mol of carbon dioxide ($CO_2$) for the production of 1 mol of methanol. While this leads to a high carbon conversion a considerable proportion of the hydrogen is lost as a purge stream. Assuming that hydrogen derives from renewable energy sources and carbon dioxide derives from an offgas source the hydrogen has the greatest influence on the economy of the relevant process.

SUMMARY

In respect of the production of methanol from synthesis gas having a high proportion of carbon dioxide there is therefore a need for improving existing processes.

It is an object of the present invention to provide a process for producing methanol which at least partially overcomes the disadvantages of the prior art.

It is a further object of the present invention to provide a process for producing methanol which allows for savings to be made in respect of the energy required for the process, in particular for operating gas compressors.

It is a further object of the present invention to provide a process for producing methanol which allows for savings to be made in respect of the plant parts required for the process, especially with regard to the number of required compressor stages.

It is a further object of the present invention to provide a process for producing methanol which very largely avoids hydrogen losses via a purge gas stream.

It is a further object of the present invention to provide a process for producing methanol which reduces catalyst loading via a high water partial pressure in the catalyst bed and extends the lifetime of the catalysts used.

It is a further object of the present invention to provide a process for producing methanol which reduces the amount of synthesis gas to be recycled in a synthesis circuit to the greatest possible extent.

It is a further object of the present invention to provide a plant for producing methanol which at least partially achieves at least one of the abovementioned objects.

The independent claims provide a contribution to the at least partial achievement of at least one of the abovementioned objects. The dependent claims provide preferred embodiments which contribute to the at least partial achievement of at least one of the objects. Preferred embodiments of constituents of a category according to the invention are, where relevant, likewise preferred for identically named or corresponding constituents of a respective other category according to the invention.

The terms "having", "comprising" or "containing" etc. do not preclude the possible presence of further elements, ingredients etc. The indefinite article "a" does not preclude the possible presence of a plurality.

The abovementioned objects are at least partially solved by a process for producing methanol comprising the following process steps, wherein these need not necessarily be performed in the recited sequence:

a) providing an input gas comprising carbon oxides and hydrogen ($H_2$), wherein the proportion of carbon dioxide ($CO_2$) in the input gas, based on the total amount of the carbon oxides, is at least 80% by volume;

b) introducing the input gas as a first fresh gas stream into a first compressor stage for precompression of the first fresh gas stream to obtain a second fresh gas stream;

c) introducing a recycle gas stream and the second fresh gas stream into a second compressor stage for compression of the recycle gas stream and the second fresh gas stream to synthesis pressure to obtain a synthesis gas stream;

d) catalytically converting the synthesis gas of the synthesis gas stream in a plurality of serially arranged reactor stages at synthesis pressure to obtain a product stream comprising methanol and unreacted synthesis gas per reactor stage;

e) cooling the product stream obtained per reactor stage for condensation and separation of methanol from unreacted synthesis gas and introducing unreacted synthesis gas into a respective subsequent stage of the serially arranged reactor stages;

f) withdrawing unreacted synthesis gas from at least one of the reactor stages as a recycle gas stream for introduction of the recycle gas stream into the second compressor stage according to step c).

According to the invention the recycle gas is introduced into the second compressor stage together with the precompressed second fresh gas stream. The catalytic conversion of the synthesis gas in a plurality of serially arranged reactor stages reduces the recycle gas amount. This allows recycle gas stream withdrawn from one or more reactor stages to be supplied directly to the second compressor stage (together with the second fresh gas stream), as a result of which the total compressor power required for the process is surprisingly reduced.

In each reactor stage synthesis gas is converted into a product stream comprising methanol. This is a crude methanol which may contain not only methanol itself but also water and further condensable by-products. The water content of the crude methanol increases with the concentration of carbon dioxide in the input gas.

Methanol is separated from the remaining synthesis gas stream by cooling and consequent condensation so that predominantly unreacted synthesis gas remains in the gas phase, Said gas is introduced into the respective subsequent stage of the serially arranged reactor stages. As is obvious to a person skilled in the art the last of the serially arranged reactor stages is an exception. Unreacted synthesis gas withdrawn from the last of the reactor stages arranged in series is introduced into the second compressor stage as a recycle gas stream.

A certain proportion of the recycle gas stream is optionally separated from the recycle gas stream as a purge gas stream. In this case unreacted synthesis gas is at least partially withdrawn from at least one of the reactor stages as a recycle gas stream for introduction of the recycle gas stream into the second compressor stage according to step c).

According to step e) methanol is at least partially separated from unreacted synthesis gas by cooling and condensation from the obtained product stream. A complete separation of methanol by cooling and condensation from unreacted synthesis gas is sought in order to shift the reaction equilibrium to the side of the product (methanol).

A preferred embodiment of the process according to the invention is characterized in that after the withdrawing according to step f) the recycle gas stream is introduced into the second compressor stage without preceding compression.

It is preferable when the recycle gas stream is supplied to the second compressor stage directly and without the use of a recycle gas compressor, i.e. without the use of a further compressor stage for compressing the recycle gas. This not only reduces the total required compressor power for the process (reduction in OPEX). It also makes it possible to omit acquisition of a recycle gas compressor, thus also reducing the CAPEX costs for the process. The entire methanol synthesis in this case requires only two compressor stages, namely the first compressor stage for compressing the first fresh gas to produce the second fresh gas and the second compressor stage for compressing the second fresh gas, together with the recycle gas, to synthesis pressure to produce the synthesis gas.

A preferred embodiment of the process according to the invention is characterized in that according to step e) unreacted synthesis gas is completely introduced into the respective subsequent stage of the serially arranged reactor stages.

This comprises introducing the maximum possible amount of unreacted synthesis gas into the respective subsequent stage of the serially arranged reactor stages, which is presently to be understood as meaning "completely". As is known to those skilled in the art in the present case, a small part of the unreacted synthesis gas is always dissolved in the condensate (methanol). This small part accordingly cannot be introduced into the following reactor stage.

In this embodiment unreacted synthesis gas is generated only in the last of the serially arranged reactor stages and the amount of the recycle gas stream is reduced to a minimum.

A preferred embodiment of the process according to the invention is thus further characterized in that according to step f) unreacted synthesis gas is withdrawn as a recycle gas stream from the last of the plurality of serially arranged reactor stages, in particular exclusively withdrawn from the last of the plurality of serially arranged reactor stages.

A preferred embodiment of the process according to the invention is characterized in that the recycle gas stream and the second fresh gas stream are merged and introduced into the second compressor stage as a combined gas stream.

In this case both streams are initially mixed after merging and subsequently introduced into the second compressor stage as a combined gas stream.

A preferred embodiment of the process according to the invention is characterized in that the input gas has a stoichiometry number SN of 1.5 to 2.2, wherein $$SN = \frac{n(H_2) - n(CO_2)}{n(CO) + n(CO_2)}, \text{ with } n \text{ in [mol]}.$$

The process according to the invention is suitable especially for highly substoichiometric synthesis gases having a high carbon dioxide content to slightly substoichiometric input gases having a high carbon dioxide content.

In this case, it is preferred that the input gas has a stoichiometry number SN of 1.5 to 1.9, preferably of 1.6 to 1.8.

Investigations have surprisingly shown that compositions according to the abovementioned stoichiometry number allow a further reduction of the total required compressor power of the process according to the invention. When this stoichiometry number is less than 2 and when the input gas comprises for example exclusively carbon dioxide based on the carbon oxides then the ratio of hydrogen to carbon dioxide is smaller than the (ideal) stoichiometric ratio of 3 to 1. Carbon dioxide is thus present in excess. This improves the hydrogen conversion which also has a positive effect on the overall economy of the process. This is because it can be assumed that hydrogen is always the more expensive raw material compared to carbon dioxide, which is why hydrogen has a decisive influence on the economy of the process.

A preferred embodiment of the process according to the invention is characterized in that for a recirculation rate R defined as $$R = \frac{\text{Volume flow(recycle gas stream)}}{\text{Volume flow(second fresh gas stream)}},$$

$0.155 \le R \le 1.25$.

Volume flows are in each case to be understood as meaning standardized volume flows based on the physical standard state of the respective gas at 0° C. and 1.01325 bar absolute pressure (standard volume flow).

Compared to known processes the recirculation rates in the process according to the invention are very low through the use of a plurality of serially arranged reaction stages with intermediate condensation.

It is further preferred when for the recirculation rate R: $0.1 \le R \le 0.5$.

Investigations have surprisingly shown that especially when using substoichiometric input gases, i.e. input gases having a stoichiometry number of less than 2, the recirculation rate may be further reduced while maintaining a constant high hydrogen conversion. When the amount of the recycle gas stream is further reduced, especially to values markedly lower than 1, the total required compressor power also falls correspondingly.

A preferred embodiment of the process according to the invention is characterized in that based on the input gas a carbon dioxide conversion of at least 80 mol % is achieved over the entirety of the plurality of serially arranged reactor stages. Based on the input gas the proportion of the carbon dioxide converted over all reactor stages, accounting for the recycle gas stream and thus considered as an overall balance, is preferably at least 80 mol %. It is particularly preferable when the carbon dioxide conversion is at least 90 mol %, more preferably at least 95 mol % and more preferably at least 98 mol %.

Since carbon dioxide is in most cases a cheap raw material, conversions of at least 80 mol % are economically acceptable and thus preferred, higher conversions being more preferred since disposal of unconverted carbon dioxide then becomes less of an issue.

The hydrogen conversion is preferably at least 95 mol %, more preferably at least 98 mol % or at least 99 mol %, It is preferable to achieve the highest possible hydrogen conversion since hydrogen is in many cases, in contrast to carbon dioxide, the much more costly raw material source.

A preferred embodiment of the process according to the invention is characterized in that the plurality of serially arranged reactor stages comprises a number of 2 to 8 reactor stages.

The optimal number of reactor stages depends on a multiplicity of factors such as the methanol amount to be produced, the conversion per reactor stage, composition of the input gas and in some cases further factors. Generally, CAPEX costs increase with the number of reactor stages and the amount of the recycle gas stream decreases, thus resulting in particularly high savings in respect of compressor power.

Conversely CAPEX costs decrease with a decreasing number of reaction stages but the amount of the recycle gas stream increases, thus reducing savings in respect of compressor power.

The plurality of serially arranged reactor stages therefore preferably comprises a number of 3 to 5 reactor stages, particularly preferably a number of 4 reactor stages. This achieves an optimal compromise in respect of CAPEX costs and savings in compressor power.

The objects of the invention are further at least partially achieved by a plant for producing methanol comprising the following plant elements arranged in fluid connection with one another:

a first compressor stage for precompression of a first fresh gas comprising carbon oxides and hydrogen ($H_2$) to produce a second fresh gas;

a second compressor stage for compression of the second fresh gas and a recycle gas to afford a synthesis gas at synthesis pressure arranged downstream of the first compressor stage;

a plurality of serially arranged reactor units for producing a product stream comprising methanol and unreacted synthesis gas from synthesis gas arranged downstream of the second compressor stage, wherein each of the reactor units comprises a reactor comprising a catalyst bed,
a heat exchanger for cooling the product stream and
a separator for separating methanol from unreacted synthesis gas, wherein each of the reactor units comprises an outlet for withdrawing methanol and each of the reactor units comprises an outlet for supplying unreacted synthesis gas to a respective downstream reactor unit and/or an outlet for supplying unreacted synthesis gas as recycle gas to the second compressor stage, wherein a feed for introducing the recycle gas into the second compressor stage is arranged between the first and second compressor stage.

A production unit for producing an input gas comprising hydrogen ($H_2$) and carbon oxides is arranged upstream of the plant according to the invention. Based on the total amount of the carbon oxides the input gas comprises a proportion of at least 80% by volume of carbon dioxide ($CO_2$). The input gas is supplied to the plant according to the invention as the first fresh gas.

A preferred embodiment of the plant according to the invention is characterized in that no compressor stage for precompression of the recycle gas before introduction into the second compressor stage is arranged between the outlet for supplying unreacted synthesis gas to the second compressor stage as recycle gas and the feed for introducing the recycle gas into the second compressor stage.

It is preferable when the unreacted synthesis gas is directly supplied to the second compressor stage as recycle gas after withdrawal from a reactor unit. In this case no additional compressor stage for compressing the recycle gas before supply thereof to the second compressor stage is provided between the outlet of the reactor unit and the feed to the second compressor unit.

A preferred embodiment of the plant according to the invention is characterized in that an outlet for supplying unreacted synthesis gas to the second compressor stage as recycle gas is arranged on the last of the plurality of serially arranged reactor units, preferably exclusively on the last of the plurality of serially arranged reactor units.

It is preferable when all reactor units with the exception of the last of the serially arranged reactor units have an outlet for supplying unreacted synthesis gas from a reactor unit to a respective subsequent reactor unit. Only the last of the serially arranged reactor units has an outlet for supplying unreacted synthesis gas from a reactor unit to the second compressor stage as recycle gas. This reduces the amount of the recycle gas to a minimum.

The objects of the invention are moreover at least partially solved by the use of the plant according to the invention in a process according to the invention.

BRIEF DESCRIPTION OF THE DRAWINGS

For a further understanding of the nature and objects for the present invention, reference should be made to the following detailed description, taken in conjunction with the accompanying drawings, in which like elements are given the same or analogous reference numbers and wherein.

DESCRIPTION OF THE PREFERRED EMBODIMENTS

Input Gas

The input gas comprises at least hydrogen ($H_2$) and carbon oxides. The term "carbon oxides" subsumes the compounds carbon monoxide (CO) and carbon dioxide ($CO_2$). Based on the total amount of the carbon oxides the input gas has a carbon dioxide proportion of at least 80% by volume. The input gas thus has a high carbon dioxide content. In one example the input gas comprises at least 90% by volume of carbon dioxide, or at least 95% by volume, or at least 98% by volume, or at least 99% by volume, based on the carbon oxides. In one example the input gas comprises exclusively carbon dioxide based on the carbon oxides. Such an input gas does not comprise any carbon monoxide or it comprises carbon monoxide only in traces.

The input gas may derive from any source known to those skilled in the art. The carbon dioxide of the input gas preferably derives from an off-gas source. The hydrogen of the input gas preferably derives from a water electrolysis plant, wherein the electric current for this plant has preferably been produced by a renewable energy source such as water power, wind power or photovoltaic.

In a further example the input gas derives from a reforming process. This input gas comprising hydrogen and carbon oxides is produced by reforming of a raw material comprising hydrocarbons such as methane or natural gas. The reforming process may comprise one or more steps such as steam reforming, partial oxidation or auto-thermal reforming. The reforming product was preferably further converted in a water gas shift reaction. In this case, carbon monoxide and water are converted to give carbon dioxide and hydrogen and the input gas having a high carbon dioxide content is thus obtained.

Independently of the source from which it derives the input gas may be produced at a temperature between 400° C. and 1200° C. and/or at a pressure between 10 and 60 bar. In addition to the abovementioned constituents the input gas may also contain different amounts of inert constituents such as methane or nitrogen. Inert constituents are in particular to be understood as meaning constituents inert under the conditions of methanol synthesis, i.e. constituents which are not converted into methanol or (undesired) by-products under the conditions of methanol synthesis.

The input gas is typically cooled to below the dew point of steam to condense out water before it is used as the first fresh gas in the process according to the invention. The input gas is especially cooled to below 100° C., preferably to below 60° C. and more preferably to 40° C. or less to separate water from the input gas after condensation. The first fresh gas is thus especially free or largely free from water.

Methanol

When reference is made to "methanol" in the context of the subject matter of the invention this is generally to be understood as meaning a crude methanol which may contain not only methanol itself but also water and further condensable by-products. This crude methanol is supplied to a purification to produce pure methanol in processes or plants arranged downstream of the process according to the invention or the plant according to the invention.

Compressor Stage

When reference is made to a "compressor stage" in the context of the subject matter of the invention this is to be understood as meaning either a process step in which a gas amount is compressed from a starting pressure $p_1$ to a final pressure $p_2$ (where $p_2 > p_1$) in one step or an apparatus unit suitable for compressing a gas amount from a starting pressure $p_1$ to a final pressure $p_2$ (where $p_2 > p_1$) in one step. The quotient of $p_2$ and $p_1$ describes the compression ratio of the respective compressor stage.

A "compressor" or a "compressor unit" may comprise a plurality of compressor stages, wherein the compression of $p_1$ to $p_2$ is then carried out in a plurality of steps, wherein each of the steps has a defined compression ratio.

In one example a plurality of compressor stages may be integrated into one compressor, wherein this compressor preferably comprises an intermediate cooling after the first and/or second compressor stage. In a further example two serially arranged compressors each have only one compressor stage.

First Compressor Stage, First Fresh Gas

The first fresh gas is supplied to the first compressor stage. The first compressor stage performs a compression of the first fresh gas to obtain a second fresh gas. The second fresh gas has a higher pressure than the first fresh gas.

In one example the first fresh gas has a pressure which at least largely corresponds to the pressure of the input gas, for example a pressure of 10 to 60 bar, preferably a pressure of 25 to 45 bar and more preferably a pressure of 20 to 40 bar.

Second Compressor Stage, Second Fresh Gas

In one example the second fresh gas has a pressure of 50 to 70 bar and preferably of 60 to 70 bar.

The second fresh gas, together with the recycle gas, is supplied to the second compressor stage and compressed to obtain the synthesis gas required for the catalytic conversion to methanol. Compared to the second fresh gas and/or the recycle gas the synthesis gas has a relatively high pressure.

In one example the synthesis gas has a pressure of 60 to 120 bar, preferably a pressure of 70 to 100 bar and more preferably a pressure of 80 to 90 bar.

Synthesis Pressure

In the second compressor stage the second fresh gas and the recycle gas are compressed to synthesis pressure especially as a combined gas stream. Synthesis pressure is the pressure required for the methanol synthesis which the synthesis gas should have for example upon introduction into the first of the plurality of reactor stages. In one example the synthesis pressure corresponds substantially to the pressure of the synthesis gas of for example 60 to 120 bar, preferably of 70 to 100 bar and more preferably of 80 to 90 bar.

Catalytic Conversion

The synthesis gas is subjected to catalytic conversion into methanol in the reactor stages.

The temperature of the synthesis catalyst is suitably from 180° C. to 300° C., preferably having a peak temperature of not more than 280° C. The synthesis gas enters a reactor stage preferably at a temperature of 200° C. to 250° C. and exits a reactor stage again preferably at a temperature of 220° C. to 270° C.

The fixed bed catalyst used for the methanol synthesis is preferably a copper-based catalyst. Especially suitable are copper-based catalysts comprising compounds such as zinc oxide, aluminum oxide, chromium oxide, titanium oxide, zirconium oxide (zircon) and/or magnesium oxide.

Suitable reactor types are water-cooled reactors which use boiling boiler feed water for cooling or gas-cooled reactors in which cooling is affected by unconverted synthesis gas which is thus heated and may be introduced into the next reactor stage in a preheated state.

Reactor Stage, Reactor Unit

In the context of the subject matter of the invention a "reactor stage" is in principle to be understood as meaning a process step and/or an apparatus which is suitable for performing a chemical reaction. In the context of the subject matter of the invention a "reactor unit" is to be understood as meaning an apparatus suitable for performing a chemical reaction.

A reactor stage or a reactor unit may contain not only the actual reactor but especially also a heat exchanger arranged downstream of the reactor for cooling the product stream, in particular for condensation of methanol. A reactor stage or a reactor unit further comprises in particular a separator, for example for separating condensed methanol from unconverted synthesis gas. Outlets of a reactor stage or a reactor unit for withdrawing unreacted synthesis gas which in further steps is supplied to the following reactor stage or reactor unit or is supplied to the second compressor stage as recycle gas are located in particular on the separator part of the reactor stage or reactor unit.

The product stream is preferably cooled by heat exchangers to a temperature of less than 50° C. to condense methanol and separate it from unreacted synthesis gas in the separator.

Product Stream

Catalytic conversion of the synthesis gas over a fixed bed catalyst at elevated temperature affords a product stream comprising methanol (crude methanol, comprising methanol, water and condensable by-products) and unreacted synthesis gas.

When using an input gas having a high carbon dioxide content water is necessarily obtained as a significant constituent in the crude methanol. Since steam results in successive deactivation of the synthesis catalyst especially at high partial pressures it is separated from unreacted synthesis gas by cooling and separation together with methanol itself and condensable by-products. Condensable by-products are for example dimethyl ether, methyl formate, acetone, ethanol and higher alcohols.

Unreacted Synthesis Gas

Synthesis gas supplied to the respective reactor stage is only ever partially converted into methanol according to the thermodynamic equilibrium constant which is a function of temperature. Unconverted synthesis gas is unreacted synthesis gas. This is either supplied to a subsequent stage of the plurality of serially arranged reactor stages or is supplied to the second compressor stage as recycle gas.

Recycle Gas

The proportion of the unreacted synthesis gas which after exiting a reactor stage is not supplied to a subsequent stage of the plurality of reactor stages is in particular recycled to the second compressor stage as recycle gas.

A portion of the recycle gas stream may be diverted from the recycle gas stream as a purge stream. In the methanol synthesis hydrogen and carbon oxides are consumed at the catalyst bed of a reactor stage. Constituents inert under the conditions of methanol synthesis such as nitrogen, argon or methane are however not consumed and may accumulate in the synthesis circuit over longer periods. Accumulation of inert gas constituents is not desired and consequently in particular a portion of the recycle gas stream is diverted from the synthesis circuit as a purge stream. The synthesis circuit is formed at least by the second compressor stage, the plurality of reactor stages and the gas streams between these elements.

Hydrogen is typically recovered from the purge stream, for example via a pressure swing adsorption apparatus or using a membrane system. Hydrogen recovered from the purge stream may be supplied to the first fresh gas stream for example.

It is preferable when the recycle gas is not compressed after withdrawal from at least one of the reactor stages and before supply to the second compressor stage. In one example the recycle gas has a pressure of 60 to 80 bar, preferably a pressure of 65 bar to 75 bar.

Working Examples

The invention is more particularly elucidated hereinbelow by way of comparative examples and inventive examples without in any way limiting the subject matter of the invention. Further features, advantages and possible applications of the invention will be apparent from the following description of the working examples in connection with the drawings and the numerical examples.

Figure 1:
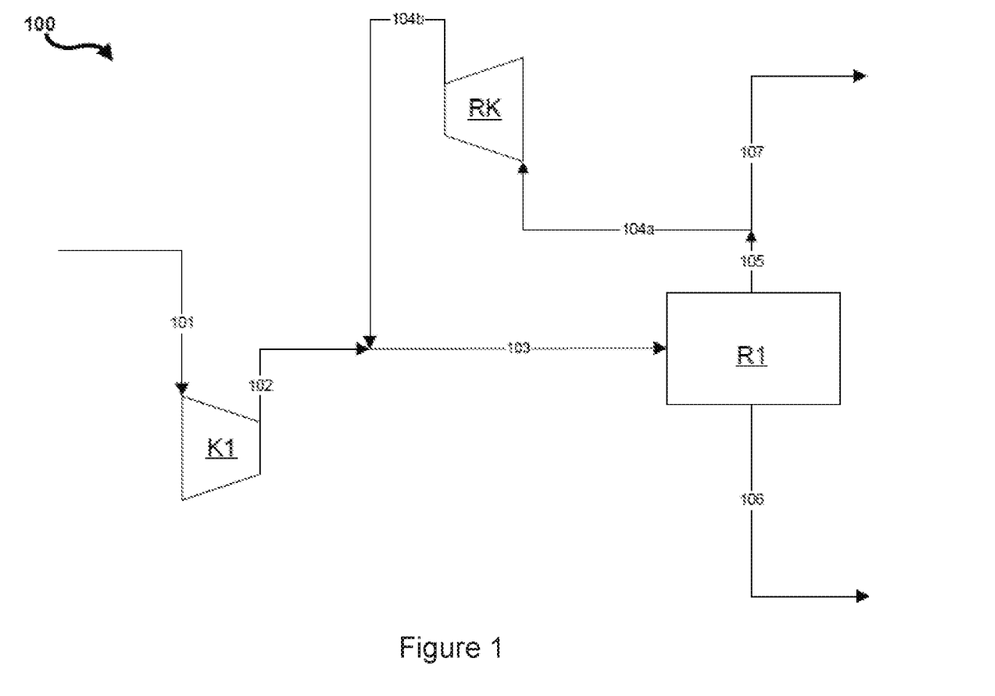
FIG. 1 shows a schematic block flow diagram of a prior art production process for methanol having a recycle gas compressor stage in the synthesis circuit.

FIG. 1 shows a much simplified schematic block flow diagram of a production process for methanol comprising a recycle gas compressor stage in a synthesis circuit comprising a single reactor stage and a single compressor stage for fresh gas.

A first compressor stage K1 is supplied with a fresh gas stream 101 at a pressure of 34 bar. The fresh gas from the fresh gas stream 101 derives from an input gas source which provides an input gas comprising exclusively carbon dioxide based on carbon oxides. Due to the molar ratio of carbon dioxide to hydrogen of 3 to 1 the fresh gas from the fresh gas stream 101 has a stoichiometry number SN of 2.0. The fresh gas stream 101 is compressed by the first compressor stage K1, thus affording a second fresh gas stream 102 on the pressure side of the compressor stage K1. The second fresh gas stream 102 is combined with the recycle gas stream 104*b*, thus resulting in a combined gas stream referred to here as synthesis gas stream 103. The compression by compressor stage K1 has the result that the synthesis gas stream 102 has a pressure of 85.0 bar at the inlet to the reactor stage R1, In the reactor stage R1 synthesis gas from the synthesis gas stream 102 is converted into methanol over a copper-based fixed bed catalyst having a catalyst volume of 16.8 m$^3$. The pressure at the reactor outlet of the reactor of R1 is 81.2 bar. The reaction is incomplete, thus affording a stream of unreacted synthesis gas 105 which is partially passed as recycle gas stream 104*a* to the recycle gas compressor stage RK and compressed to afford recycle gas stream 104*b* on the pressure side of the recycle gas compressor stage RK. A portion of the unreacted synthesis gas 105 is removed from the synthesis circuit as purge stream 107 in order to avoid accumulation of inert constituents and of by-products of the methanol synthesis, Reactor stage R1 comprises not only the actual reactor but also a heat exchanger for cooling the product stream and a separator. Cooling of the product stream and condensation of methanol in the separator affords a methanol-containing product stream 106. The methanol is in the form of crude methanol and in order to obtain pure methanol is supplied to a workup suitable according to the required purity (not shown).

In the comparative example of FIG. 1 the carbon dioxide conversion is 98.5% and the hydrogen conversion is 98.8%.

In the comparative example of FIG. 1 the recirculation rate R, i.e. the ratio of the amount of recycle gas 104*a* or 104*b* to fresh gas 102, is R=3.5, The recycle gas amount to be compressed by the recycle gas compressor stage thus corresponds to 3.5 times the fresh gas amount in each case based on the standard volume streams of recycle gas and fresh gas. At a production of 344 tons of crude methanol per day (t/d) (of which 217.5 t/d is methanol and the remainder is essentially water) the comparative example of FIG. 1 requires a compressor power of 1162 kW for K1 and 325 kW for RK, thus corresponding to a total compressor power of 1487 kW.

Figure 2:
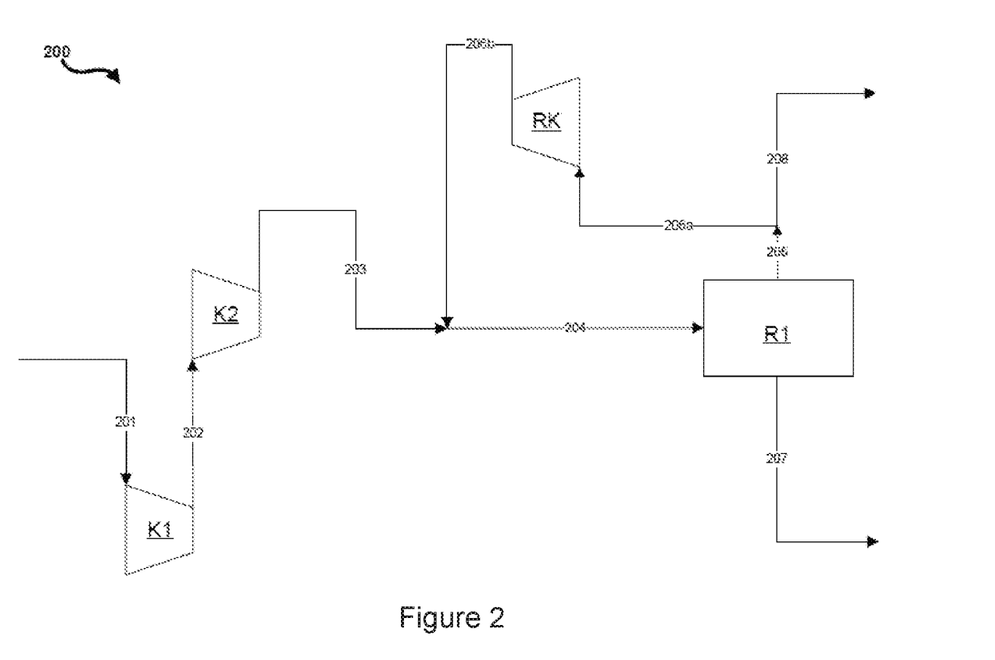
FIG. 2 shows a schematic block flow diagram of a prior art production process for methanol having a recycle gas compressor stage in the synthesis circuit.

FIG. 2 shows a much simplified schematic block flow diagram of a production process for methanol comprising a recycle gas compressor stage in a synthesis circuit comprising a reactor stage and two serially arranged compressor stages for fresh gas. The process of FIG. 2 thus differs from the process of FIG. 1 only in the use of an additional compressor stage for fresh gas.

A first compressor stage K1 is supplied with a first fresh gas stream 201 at a pressure of 34 bar. The fresh gas from the fresh gas stream 201 derives from an input gas source which provides an input gas comprising exclusively carbon dioxide based on carbon oxides. Due to the molar ratio of carbon dioxide to hydrogen of 3 to 1 the fresh gas from the fresh gas stream 101 has a stoichiometry number SN of 2.0. The fresh gas stream 201 is compressed by the first compressor stage K1, thus resulting in a second fresh gas stream 202 having a pressure of 65.0 bar on the pressure side of the compressor stage K1. The second fresh gas stream 202 is compressed by the second compressor stage K2 to result in a third fresh gas stream 203 on the pressure side of K2. The third fresh gas stream 203 is combined with recycle gas stream 206*b*, thus resulting in a combined gas stream referred to here as synthesis gas stream 204. The compression by compressor stage K2 has the result that the synthesis gas stream 204 has a pressure of 85.0 bar at the inlet to the reactor stage R1. In the reactor stage R1 synthesis gas from the synthesis gas stream 204 is converted into methanol over a copper-based fixed bed catalyst having a catalyst volume of 16.8 m$^3$. The pressure at the reactor outlet is 81.2 bar. The reaction is incomplete, thus affording a stream of unreacted synthesis gas 205 which is partially passed as recycle gas stream 206*a* to the recycle gas compressor stage RK and compressed to afford recycle gas stream 206b on the pressure side of the recycle gas compressor stage RK. A portion of the unreacted synthesis gas 205 is removed from the circuit as purge stream 208 in order to avoid accumulation of inert constituents. Reactor stage R1 comprises not only the actual reactor but also a heat exchanger for cooling the product stream and a separator. Cooling of the product stream and condensation of methanol in the separator affords a methanol-containing product stream 207. The methanol is in the form of crude methanol and according to the required purity is supplied to a suitable workup to obtain pure methanol (not shown).

In the comparative example of FIG. 2 the carbon dioxide conversion is likewise 98.5% and the hydrogen conversion is likewise 98.8%.

In the comparative example of FIG. 2 the recirculation rate R, i.e. the ratio of the amount of recycle gas 206a or 206b to fresh gas 203, is likewise R=3.5, At a production of 344 tons of crude methanol per day (t/d) (of which 217.5 t/d is methanol and the remainder is essentially water) the comparative example of FIG. 2 requires a compressor power of 1090 kW for K1 and K2 together and of 325 kW for RK, thus corresponding to a total compressor power of 1415 kW. The total compressor power is thus somewhat lower than in the comparative example of FIG. 1 but three compressor stages K1, K2 and RK are required therefor, thus increasing the CAPEX costs for the plant.

Figure 3:
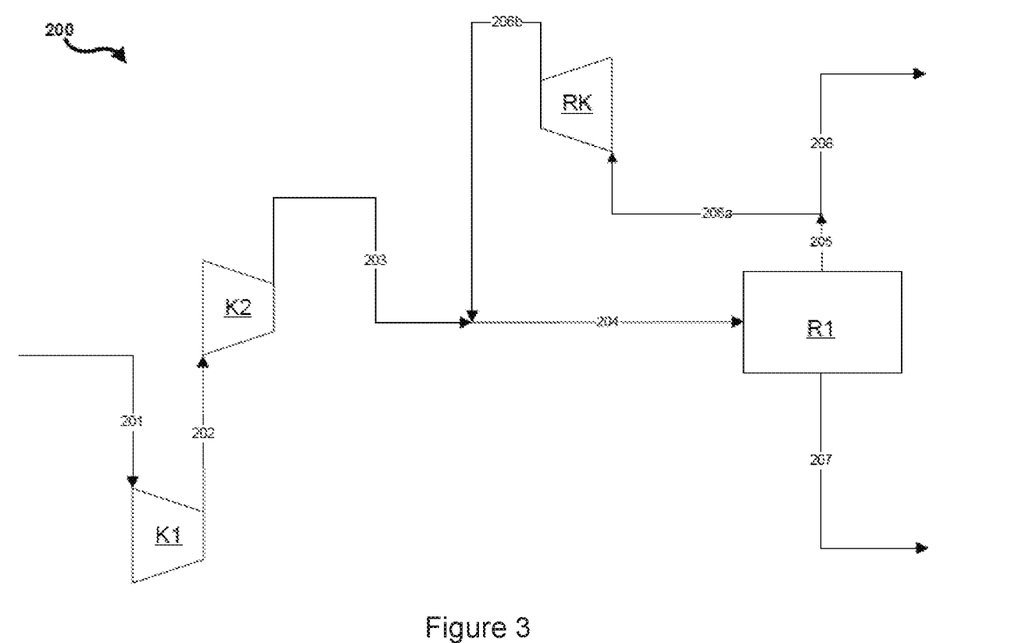
FIG. 3 shows a schematic block flow diagram of an inventive production process for methanol having a plurality of serially arranged reactor stages without a recycle gas compressor stage in the synthesis circuit, in accordance with one embodiment of the present invention.

FIG. 3 shows a much simplified schematic block flow diagram of an inventive production process for methanol without a recycle gas compressor stage in the synthesis circuit, wherein the synthesis circuit comprises a plurality of serially arranged reactor stages.

A first compressor stage K1 is supplied with a fresh gas stream 301 at a pressure of 34.0 bar. The fresh gas from the fresh gas stream 301 derives from an input gas source which provides input gas comprising exclusively carbon dioxide based on carbon oxides. Due to the molar ratio of carbon dioxide to hydrogen of 3 to 1 the fresh gas from the fresh gas stream 301 has a stoichiometry number SN of 2.0. The first fresh gas stream 301 is compressed by the first compressor stage K1, thus affording a second fresh gas stream 302 having a pressure of 65.0 bar on the pressure side of the compressor stage K1. The second fresh gas stream 302 is merged with recycle gas stream 305, thus resulting in a combined gas stream 303 which is introduced into a second compressor stage K2 to be compressed to a pressure of 85.0 bar. This results on the pressure side of the second compressor stage in a gas stream having synthesis pressure, referred to here as synthesis gas stream 304.

The synthesis gas stream 304 is introduced into a first of altogether four serially arranged reactor stages R1 to R4. In the first reactor stage R1 synthesis gas 304 is converted into methanol over a copper-based fixed bed catalyst having a catalyst volume of 4.2 m$^3$.

The reactor stages R2, R3 and R4 each have a catalyst volume of 4.2 m$^3$ of the same copper-based catalyst, thus resulting in a total catalyst volume of 16.8 m$^3$ which corresponds to the catalyst volume of the single reactor stage in the comparative examples according to FIG. 1 and FIG. 2.

The incomplete conversion of the synthesis gas 304 in reactor stage R1 affords a stream of unreacted synthesis gas 306a which is introduced into the subsequent stage of the serially arranged reactor stages, in the present case into reactor stage R2. Reactor stage R1 and further reactor stages R2 to R4 comprise not only the actual reactor but also a heat exchanger for cooling the product stream and a separator. Cooling of the product stream and condensation of methanol in the separator affords a product stream 307a in R1.

Analogously to the catalytic conversion in R1, unreacted synthesis gas 306a is converted into methanol and by-products in reactor stage R2, thus affording a further product stream 307b. Synthesis gas not reacted in the conversion over the copper-based catalyst of R2 is in turn introduced into the following reactor stage R3 to afford a product stream 307c and unreacted synthesis gas 306c. A small proportion of unreacted synthesis gas R2 is always dissolved in the condensate (methanol) and is not available for the next reactor stage. Unreacted synthesis gas 306c is introduced into the last of the serially arranged reactor stages R4 to obtain a further product stream 307d. The product streams 307a to 307d are merged to afford a total product stream 307. Total product stream 307 comprises crude methanol which according to the required purity is supplied to a suitable workup to obtain pure methanol (not shown).

The pressure at the reactor outlet of the reactor stage R4 is 74.9 bar. The pressure drop over all reactor stages is thus 10.1 bar. Synthesis gas 306d not reacted in the last reactor stage is directly recycled as recycle gas stream 305 to the second fresh gas stream 302 and merged with said stream. In the example according to FIG. 3 a portion of the unreacted synthesis gas withdrawn in the last reactor stage R4 is diverted as a purge gas stream to avoid accumulation of inert constituents and by-products in the recycle gas stream 305.

In the example of FIG. 3 the carbon dioxide conversion is 98.3% and the hydrogen conversion is 98.6%. The conversions are therefore comparable with the conversions according to the comparative examples (setup of FIGS. 1 and 2).

In the example of FIG. 3 the recirculation rate R, i.e. the ratio of the amount of recycle gas 305 to fresh gas 302, is R=0.9. The recycle gas amount 305 thus corresponds to 90% of the fresh gas amount 302 in each case based on the standard volume streams of recycle gas and fresh gas. At identical carbon and hydrogen conversion the recirculation rate is thus a factor of approximately 3.9 smaller than in the comparative examples as a result of the higher conversion and the intermediate condensation of products in the plurality of reactor stages (R1 to R4).

At a production of 344 tons of crude methanol per day (t/d) (of which 217.5 t/d is methanol and the remainder is essentially water) the example of FIG. 3 requires a compressor power of 783 kW for K1 and 601 kW for K2 which corresponds to a total compressor power of 1384 kW. The total compressor power is thus significantly lower than in the comparative example according to FIG. 1 and also somewhat lower than in the comparative example according to FIG. 2. However, the configuration according to the example of FIG. 3 requires in total only two compressor stages in comparison with the configuration of the comparative example of FIG. 2. In the comparative example of FIG. 1 in turn the total compressor power is significantly higher with an identical number of compressor stages.

The surprising effect achieved by the configuration according to the example of FIG. 3 is even more strongly brought to bear when the input gas has a stoichiometry number SN of less than 2 as shown hereinbelow for a stoichiometry number SN=1.7. In this second example, too, the input gas comprises exclusively carbon dioxide based on carbon oxides. To achieve a relatively low stoichiometric number the volume flow of carbon dioxide is relatively high compared to the previous examples, thus causing the fresh gas to have a carbon dioxide excess.

In this second example which otherwise employs the configuration of the example of FIG. 3 the total compressor output is 1251 kW and thus 133 kW lower than in the first inventive example where SN=2.0. The substoichiometric fresh gas ($H_2$ in deficiency and carbon dioxide in excess) surprisingly further reduces the recirculation rate to 0.41, i.e., less than half of the recycle gas 305 relative to fresh gas 302 is required to produce the same crude methanol amount 307 of 344 tons per day (of which 217.5 t/d is methanol and the remainder is essentially water) coupled with a high hydrogen conversion. The low recycle gas amount 305 also results in a low required purge gas amount which in turn entails hydrogen recovery savings. In the second example the hydrogen conversion is 98.8% and is thus comparable with all previous examples. The carbon conversion is slightly lower at 89.5% but due to the low costs of this raw material, especially when said material derives from off-gases sources, this has no effect on the overall economy of the process.

The results recited above are summarized to give an overview in the following table.

|  | Comparative example 1 (FIG. 1) | Comparative example 2 (FIG. 2) | Example 1 (FIG. 3) | Example 2 (FIG. 3) |
|---|---|---|---|---|
| $H_2$ volume flow/kmol/h | 862.5 | 862.5 | 862.5 | 862.5 |
| $CO_2$ volume flow/kmol/h | 287.5 | 287.5 | 287.5 | 319 |
| SN (fresh gas) | 2.00 | 2.00 | 2.00 | 1.70 |
| First fresh gas pressure/bar | 34.0 | 34.0 | 34.0 | 34.0 |
| Second fresh gas pressure/bar | n/a | 65.0 | 65.0 | 65.0 |
| Synthesis gas pressure/bar | 85.0 | 85.0 | 85.0 | 85.0 |
| Outlet reactor unit (at the separator) pressure/bar | 81.2 | 81.2 | 74.9 | 78.5 |
| Catalyst volume/m$^3$ | 16.8 | 16.8 | 4 × 4.2 | 4 × 4.2 |
| Methanol produced in crude methanol/t/d | 217.5 | 217.5 | 217.5 | 217.5 |
| $CO_2$ conversion/% | 98.5 | 98.5 | 98.3 | 89.5 |
| $H_2$ conversion/% | 98.8 | 98.8 | 98.6 | 98.8 |
| Recirculation rate (recycle gas/fresh gas)/kmol/kmol | 3.5 | 3.5 | 0.9 | 0.41 |
| Power K1/kW | 1162 | 783 | 783 | 803 |
| Power K2/kW | n/a | 307 | 601 | 448 |
| RK power/kW | 325 | 325 | n/a | n/a |
| Total compressor power/kW | 1487 | 1415 | 1384 | 1251 |

Embodiments of the invention are described with reference to different types of subject-matter. In particular, certain embodiments are described with reference to process claims while other embodiments are described with reference to apparatus claims. However, it will be apparent to a person skilled in the art from the description hereinabove and hereinbelow that unless otherwise stated in addition to any combination of features belonging to one type of claim any combination of features relating to different types of subject-matter or types of claim may also be contemplated. All features may be combined to achieve synergistic effects which go beyond simple summation of the technical features.

While the invention has been represented and described in detail in the drawing and the preceding description, such a representation and description shall be considered elucidatory or exemplary and non-limiting. The invention is not limited to the disclosed embodiments. Other variations of the disclosed embodiments may be understood and executed by those skilled in the art of the field of the claimed invention from a study of the drawing, the disclosure and the dependent claims.

In the claims, the word "having" or "comprising" does not exclude further elements or steps and the indefinite article "a" or "an" does not exclude a plurality. Reference numerals in the claims should not be interpreted as limiting the scope of the claims.

LIST OF REFERENCE NUMERALS

K1 First compressor stage
K2 Second compressor stage
RK Recycle gas compressor stage
R1, R2, R3, R4 Reactor stage, reactor unit
101 First fresh gas stream
102 Second fresh gas stream
103 Synthesis gas stream
104a,b Recycle gas stream
105 Unreacted synthesis gas
106 Product stream (crude methanol)
107 Purge gas stream
201 First fresh gas stream
202 Second fresh gas stream
203 Third fresh gas stream
204 Synthesis gas stream
205 Unreacted synthesis gas
206a,b Recycle gas stream
207 Product stream (crude methanol)
208 Purge gas stream
301 First fresh gas stream
302 Second fresh gas stream
303 Combined gas stream
304 Synthesis gas stream
305 Recycle gas stream
306a,b,c,d Unreacted synthesis gas
307 Total product stream (crude methanol)
307a,b,c,d Product stream (crude methanol)
308 Purge gas stream

What is claimed is:

1. A process for producing methanol, comprising:
   a) providing an input gas comprising carbon oxides and hydrogen, wherein the proportion of carbon dioxide in the input gas, based on the total amount of the carbon oxides, is at least 80% by volume;
   b) introducing the input gas as a first fresh gas stream into a first compressor stage for precompression of the first fresh gas stream to obtain a second fresh gas stream;
   c) introducing a recycle gas stream and the second fresh gas stream into a second compressor stage for compression of the recycle gas stream and the second fresh gas stream to synthesis pressure to obtain a synthesis gas stream;
   d) catalytically converting the synthesis gas of the synthesis gas stream in a plurality of serially arranged reactor stages at synthesis pressure to obtain a product stream comprising methanol and unreacted synthesis gas per reactor stage;
   e) cooling the product stream obtained per reactor stage for condensation and separation of methanol from unreacted synthesis gas and introducing unreacted synthesis gas into a respective subsequent stage of the serially arranged reactor stages;
   f) withdrawing unreacted synthesis gas from at least one of the reactor stages as a recycle gas stream for introduction of the recycle gas stream into the second compressor stage according to step c).

2. The process according to claim 1, wherein after the withdrawing in step f) the recycle gas stream is introduced into the second compressor stage without preceding compression.

3. The process according to claim 1, wherein according to step e) unreacted synthesis gas is completely introduced into the respective subsequent stage of the serially arranged reactor stages.

4. The process according to claim 1, wherein according to step f) unreacted synthesis gas is withdrawn as a recycle gas stream from the last of the plurality of serially arranged reactor stages, in particular exclusively withdrawn from the last of the plurality of serially arranged reactor stages.

5. The process according to claim 1, wherein the recycle gas stream and the second fresh gas stream are merged and introduced into the second compressor stage as a combined gas stream.

6. The process according to claim 1, wherein the input gas has a stoichiometry number SN of 1.5 to 2.2, wherein $$SN = \frac{n(H_2) - n(CO_2)}{n(CO) + n(CO_2)}, \text{ with } n \text{ in [mol]}.$$

7. The process according to claim 6, wherein the input gas has a stoichiometry number SN of 1.5 to 1.9.

8. The process according to claim 1, wherein a recirculation rate R is defined as $$R = \frac{\text{Volume flow(recycle gas stream)}}{\text{Volume flow(second fresh gas stream)}},$$

$0.15 \leq R \leq 1.25$.

9. process according to claim 8, wherein the recirculation rate R: $0.1 \leq R \leq 0.5$.

10. The process according to claim 1, wherein based on the input gas a carbon dioxide conversion of at least 80 mol % is achieved over the entirety of the plurality of serially arranged reactor stages.

11. The process according to claim 1, wherein the plurality of serially arranged reactor stages comprises a number of 2 to 8 reactor stages.

* * * * *